US00PP15155P2

(12) United States Plant Patent
Carruth

(10) Patent No.: US PP15,155 P2
(45) Date of Patent: Sep. 21, 2004

(54) FLORIBUNDA ROSE PLANT NAMED 'WEKPALTLEZ'

(50) Latin Name: *Rosa hybrida*
Varietal Denomination: WEKpaltlez

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 10/614,612

(22) Filed: Jul. 2, 2003

(51) Int. Cl.[7] ..... A01H 5/00
(52) U.S. Cl. ..... Plt./141
(58) Field of Search ..... Plt./141

*Primary Examiner*—Anne Marie Grunberg
*Assistant Examiner*—S B McCormick-Ewoldt
(74) *Attorney, Agent, or Firm*—Christie, Parker & Hale, LLP

(57) ABSTRACT

A new variety of Floribunda rose suitable for garden decoration, having flowers of smoky chocolate orange coloration overlaid with a wash of lavender.

1 Drawing Sheet

Classification: The present invention relates to a new Rosa hybrida plant.

Variety denomination: The new plant has the varietal denomination 'WEKpaltlez'.

BACKGROUND OF THE INVENTION

This invention relates to a new and distinct variety of Floribunda Rose. It has as its seed parent an undisseminated seedling of my creation and as its pollen parent the variety known as 'HARwelcome' (U.S. Plant Pat. No. 9,161).

SUMMARY OF THE INVENTION

Among the features which distinguish the new variety from other presently available and commercial rose cultivars known to the inventor are the following combination of characteristics: its unusual smoky chocolate orange coloration overlaid with a wash of lavender, its highly glossed foliage surface, its numerous stipitate glands on the new shoots and its dark new growth. The plant has a bushy upright growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKpaltlez' may be asexually propagated by cuttings, budding and grafting. The budding and grafting successfully occurred on the plant/rootstock Rosa hybrida cv. 'Dr. Huey'.

COMPARISON WITH PARENTS

The new rose may be distinguished from its seed parent, an undisseminated seedling of my creation by the following combination of characteristics: whereas 'WEKpaltlez' bears medium sized flowers (about 6.7 to about 10.2 cm. in diameter) of unusual smoky chocolate orange coloration overlaid with a wash of lavender and with double petalage (about 17 to 27 petals), the undisseminated seedling bears significantly smaller flowers of orange-red coloration with lesser petalage (about 7 to 10 petals). The new variety is classified as a floribunda rose with a bushy upright mature growing habit, whereas the seed parent is a climbing rose with a significantly larger and more spreading mature growing habit.

The new variety may be distinguished from its pollen parent, 'HARwelcome' by the following combination of characteristics: whereas 'WEKpaltlez' bears flowers of unusual smoky chocolate orange coloration overlaid with a wash of lavender, the pollen parent bears flowers of blended orange coloration. 'WEKpaltlez' bears dark new foliage, whereas 'HARwelcome' bears significantly lighter new foliage. The new variety is classified as a floribunda rose with a bushy upright mature growing habit, whereas the pollen parent is classified as floribunda rose with a significantly smaller and more compact mature growing habit.

BRIEF DESCRIPTION OF THE ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of June. Phenotypic expression may vary with environmental, cultural and climatic conditions, as well as differences in conditions of light and soil.

FLOWER

The new variety usually bears its flowers in clusters of two to five or more per stem. Flowers are borne in regular rounded clusters on strong medium to long stems (about 48 to about 75 cm). Outdoors, the plant blooms abundantly and nearly continuously during the growing season. The flowers have a moderate tea fragrance.

BUD

The peduncle is about 2.4 to about 4.6 cm. in length, of average caliper (about 0.2 to about 0.3 cm. in diameter), and usually erect. It is almost entirely smooth, with some stipitate glands and few hairs. Peduncle color is between 144B and 136C often heavily suffused, especially on the side exposed to the sun, with between 183A and 187B.

Before the calyx breaks, the bud is about 1.0 to about 1.8 cm. in diameter at the widest point, about 1.4 to about 2.1 cm. in length, and ovoid to slightly globular in shape. The surface of the bud bears some foliaceous appendages and very few stipitate glands, usually with slender entire foliaceous parts extending beyond the tip of the bud about ¼ or more of its length. Bud color is between 144A and 136B often heavily suffused, especially on the side exposed to the sun, with between 187A and 183A.

The sepals are about 1.9 to about 2.4 cm. in length and about 0.6 to about 1.0 cm. in width at the widest point. The outer surface of the sepal is between 144A and 136B often heavily suffused, especially on the side exposed to the sun, with between 187A and 183A. The inner surface of the sepal is between 138B and 137B and covered with fine wooly tomentum; sepal margins are lined with some stipitate glands and hairs.

As the petals open (after the calyx breaks), the bud is about 1.7 to about 2.5 cm. in diameter at the widest point, about 2.4 to about 3.1 cm. in length, and moderately ovoid to globular in form. The color of the under surfaces of the newly opened petals is between 34A and 47A sometimes lightly overlaid near the tip of the petals with a wash of between 77A and 79A. The areas with the over wash color give a visual appearance of between 183A and 183C. At the point where the petal attaches, there is a small zone of between 1D and 154D.

The color of the upper surfaces of the newly opened petals is between 44A and 42B usually lightly overlaid with a wash of between 77A and 79A. The areas with the over wash color give a visual appearance of between 183B and 183C. At the point where the petal attaches, there is a moderately small zone of near 3C.

BLOOM

When fully open, the bloom ranges from about 6.7 to about 10.2 cm. in diameter. Petalage is double with about 17 to 27 petals and about 2 to 14 petaloids irregularly arranged. When partially open, the bloom form is somewhat high-centered to moderately globular, and the petals are somewhat tightly cupped with petal edges very slightly reflexed outward. When fully open, the outer petals are more flat to slightly cupped and the inner petals are more cupped with petal edges somewhat reflexed outward.

PETALS

The substance of the petals is moderately heavy to somewhat leathery and of medium thickness, with upper surfaces moderately satiny to slightly velvety and under surfaces mostly matte to slightly shiny. The outer petals are nearly rounded to somewhat obovate in shape with mostly mucronate to sometimes rounded apices. The inner petals are obovate in shape with mostly mucronate to sometimes rounded apices. The petals are about 2.5 to about 3.8 cm. in length and about 1.9 to about 3.6 cm. in width at the widest point. Petal margins are entire.

NEWLY OPENED FLOWER

The under surface of the outer petals is between 45C and 47C sometimes lightly overlaid near the very tip of the petals with a wash of between 77A and 79A. The areas with the over wash color give a visual appearance of between 183A and 183C. At the point where the petal attaches, there is a small zone of near 5D.

The upper surface of the outer petals is between 41B and 42D usually moderately overlaid with a wash of between 77A and 79C. The areas with the over wash color give a visual appearance of between 183B and 183C. At the point where the petal attaches, there is a moderately small zone of between 5C and 7D.

The under surface color of the intermediate and inner petals is between 42A and 47C. The upper surface color of the intermediate and inner petals is between 40B and 42D usually moderately overlaid with a wash of between 77A and 79C. The areas with the over wash color give a visual appearance of between 183B and 183C.

The general tonality of the newly opened flower is between 40B and 42D usually lightly overlaid with a wash of between 77A and 79C. The areas with the over wash color give a visual appearance of between 183B and 183C.

THREE-DAY-OLD FLOWER

The under surface of the outer, intermediate and inner petals is between 47B and 47C. At the point where the petal attaches, there is a small zone of between 5D and 9D. The upper surface of the outer, intermediate and inner petals is between 43C and 55B usually lightly overlaid with a wash of between 79C and 77C. The areas with the over wash color give a visual appearance of between 183D and 185C. At the point where the petal attaches, there is a moderately small zone of between 5D and 6D.

The general tonality of the three-day-old flower is between 43C and 55B usually lightly overlaid with a wash of between 79C and 77C. The areas with the over wash color give a visual appearance of between 183D and 185C.

On the spent bloom, the petals usually drop off cleanly.

In June in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are average in number (average about 100) and are arranged regularly about the pistils; some are mixed with petaloids. The filaments are of medium to somewhat long length (about 0.6 to about 1.1 cm.), most with anthers. Filaments are between 7B and 9B at the base lightly suffusing to near 32B in color near the top. The anthers are of medium size for the class and all open approximately at the same time. Anther color is between 23B and 183D when immature and between 163C and 200A at maturity. Pollen is somewhat abundant.

FEMALE REPRODUCTIVE ORGANS

Pistils vary in number (average about 75). The styles are very uneven, moderately short in length (about 0.3 to about 0.6 cm.), moderately thin in caliper, and loosely bunched. Stigma color is near 16C. Style color is between 53A and 60A. Ovaries are all enclosed in the calyx.

Hips are of moderately short to average length (about 1.4 to about 1.9 cm.), moderately globular to somewhat urn-shaped in form, and between 30A and 33B in color when ripe. The hip surface is very smooth with thick fleshy walls. The sepals are moderately permanent, somewhat short to medium in length, and usually straight in shape. The seeds are irregularly rounded, smooth in texture, approximately 7 to about 11 per hip, about 0.3 to about 0.5 cm. in diameter at the widest point and between 160C and 162C in color.

FOLIAGE

The compound leaves are usually comprised of three to seven or more leaflets and are borne abundantly. The seven-leaflet leaves are about 13.7 to about 15.6 cm. in length and about 10.7 to about 12.8 cm. in width at the widest point, moderately leathery to somewhat crisp in texture, and very glossy in finish. The terminal leaflets are about 5.5 to about 7.4 cm. in length and about 3.4 to about 4.5 cm. in width at the widest point, shaped moderately ovate to somewhat oval with moderately acuminate to somewhat acute apices and rounded bases. The apices sometimes veer to one side at an angle of less than 45 degrees. Their margins are usually simply serrate.

The upper surface of the mature leaf is between 147A and 131A. The under surface of the mature leaf is between 147B and 139B. The upper surface of the young leaf is between 146A and 139B, sometimes lightly suffused with between 187A and 187B. The under surface of the young leaf is between 146B and 139C, usually heavily suffused with between 187A and 187B.

The rachis is average in caliper and moderately rough. The upper side is shallowly grooved with some hairs and stipitate glands on the edges of the grooves. The under side of the rachis is moderately rough with some stipitate glands and some small prickles. The rachis color is between 146B and 144A.

The stipules are about 1.6 to about 2.1 cm. in length and moderately wide (about 0.4 to about 0.6 cm.) with medium length straight points that usually turn out at an angle of more than 45 degrees and sometimes slightly recurve toward the stem. The stipules color is between 144A and 146C sometimes lightly suffused on the side facing the sun with near 183B.

The petiole is about 1.0 to about 1.5 cm. in length and about 0.1 to about 0.2 cm in diameter at the widest point. The petiole color is between 146B and 144A.

The plant displays an average degree of resistance to powdery mildew and rust as compared to other commercial varieties grown under comparable conditions in Upland, Calif. The plant's winter hardiness and drought/heat tolerance are yet to be determined.

GROWTH

The plant has a bushy upright medium to tall growing habit (about 170 to about 210 cm. in height and about 120 to about 140 cm. spread at the widest point), with full branching. It displays very vigorous growth and the canes are of medium caliper for the class.

The color of the major stems is between 146B and 147B. They bear many large prickles that are about 0.8 to about 1.1 cm. in length. The large prickles are hooked moderately downward with a moderately long somewhat narrow oval base; prickle color is between 165B and 175A. The major stem bears few small prickles of similar shape and coloration.

The color of the branches is between 144A and 139B. They bear few large prickles which are about 0.3 to about 0.5 cm. in length and of similar shape to the large prickles on the major stems; prickle color is near 160C usually heavily suffused with between 187A and 185C. The branches bear very few small prickles of similar shape and coloration.

The color of the new shoots is between 144B and 139B often heavily suffused with between 187A and 187B. They bear many large prickles which are of similar size to the large prickles on the major stems. The large prickles are slightly angled downward; prickle color is between 187A and 187B. The shoots bear many small prickles of similar shape and coloration and numerous stipitate glands.

I claim:

1. A new and distinct Floribunda rose plant of the variety substantially as described and illustrated herein.

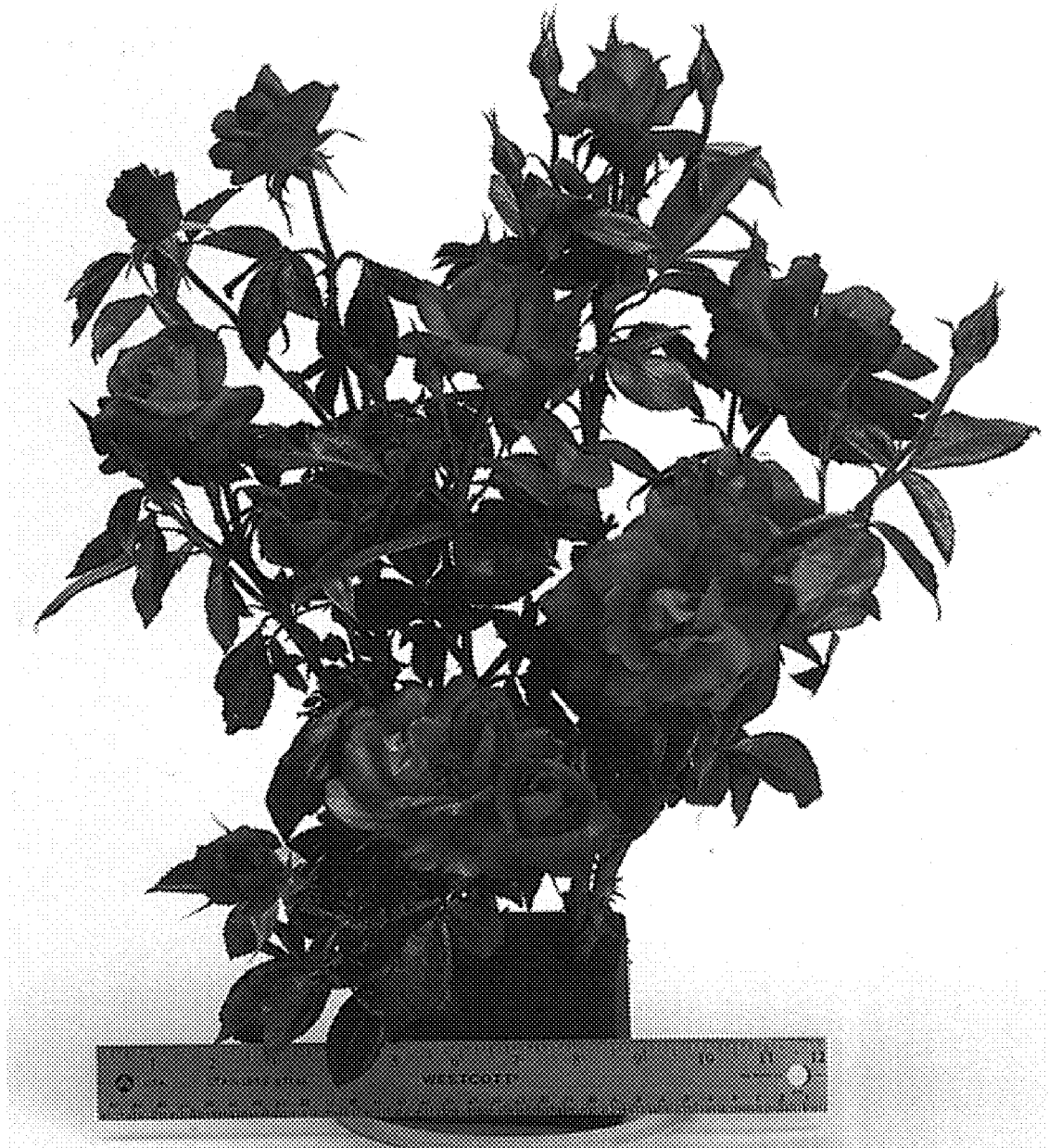

* * * * *